US010352866B1

(12) United States Patent
Arbatli

(10) Patent No.: US 10,352,866 B1
(45) Date of Patent: Jul. 16, 2019

(54) SYSTEM AND METHOD OF DETECTING WITHIN A LIQUID FLOW OF A PIPE

(71) Applicant: Mehmet Arbatli, Tomball, TX (US)

(72) Inventor: Mehmet Arbatli, Tomball, TX (US)

( * ) Notice: Subject to any disclaimer, the term of this patent is extended or adjusted under 35 U.S.C. 154(b) by 0 days.

(21) Appl. No.: 15/948,995

(22) Filed: Apr. 9, 2018

(51) Int. Cl.
| | |
|---|---|
| *G01N 21/85* | (2006.01) |
| *G01N 21/88* | (2006.01) |
| *H04B 10/60* | (2013.01) |
| *H04B 10/516* | (2013.01) |
| *A61M 1/36* | (2006.01) |
| *G01N 15/00* | (2006.01) |
| *G01N 35/10* | (2006.01) |
| *G01N 15/10* | (2006.01) |

(52) U.S. Cl.
CPC .......... *G01N 21/85* (2013.01); *A61M 1/3626* (2013.01); *G01N 21/8806* (2013.01); *H04B 10/516* (2013.01); *H04B 10/60* (2013.01); *G01N 2015/0011* (2013.01); *G01N 2015/1068* (2013.01); *G01N 2035/1018* (2013.01); *G01N 2291/02433* (2013.01)

(58) Field of Classification Search
CPC ... G01M 3/06; G01N 9/28; G01N 2001/2267; G01N 2015/1068; G01N 2035/1018; G01N 2291/02433; G01N 21/85; G01N 21/8507; G01N 21/88; G01N 21/8806; G01N 21/89; G01N 21/90; G01N 21/94; H04B 10/516; H04B 10/60; A61M 1/3626
See application file for complete search history.

(56) References Cited

U.S. PATENT DOCUMENTS

| | | | | |
|---|---|---|---|---|
| 3,812,482 | A | | 5/1974 | Clark |
| 4,112,735 | A | * | 9/1978 | McKnight .............. G01N 29/02 73/19.03 |
| 4,138,879 | A | * | 2/1979 | Liebermann .......... F25B 41/006 62/129 |
| 4,235,095 | A | * | 11/1980 | Liebermann ......... G01N 29/032 62/127 |
| 4,627,726 | A | * | 12/1986 | Turner ................... G01N 15/06 356/336 |
| 4,763,525 | A | | 8/1988 | Cobb |

(Continued)

FOREIGN PATENT DOCUMENTS

WO    WO 2017201451    11/2017

*Primary Examiner* — Gordon J Stock, Jr.
(74) *Attorney, Agent, or Firm* — Michael Diaz

(57) ABSTRACT

A system for detecting bubbles within a liquid flowing in an interior of a pipe. The system includes a transmitter emitting directed light through the liquid flowing through the pipe and a receiver for receiving the emitted directed light from the transmitter. The transmitter and receiver are affixed on opposite sides of the pipe. The system also includes a microcontroller having a modulator. The microcontroller communicates with the transmitter and receiver. The microcontroller sends a modulation protocol for emitting the directed light with a specified modulation protocol to the transmitter and receiver. The transmitter emits the directed light as modulated light based upon the modulation protocol and the receiver filters out all unmodulated light, correlates information on modulated light received from the transmitter and sends correlated light information to the microcontroller. The microcontroller determines a presence of bubbles in the liquid based on the light information received from the receiver.

19 Claims, 4 Drawing Sheets

(56) References Cited

U.S. PATENT DOCUMENTS

| | | | | |
|---|---|---|---|---|
| 5,033,858 A | * | 7/1991 | Twerdochlib | G01N 15/06 340/621 |
| 5,083,862 A | | 1/1992 | Rusnak | |
| 5,455,423 A | | 10/1995 | Mount et al. | |
| 5,960,129 A | | 9/1999 | Kleinschmitt | |
| 5,991,019 A | * | 11/1999 | Sander | G01N 21/31 356/300 |
| 6,408,679 B1 | * | 6/2002 | Kline-Schoder | A61B 8/08 73/19.03 |
| 6,457,346 B1 | * | 10/2002 | Kline-Schoder | A61B 8/08 128/916 |
| 6,463,785 B1 | * | 10/2002 | Kline-Schoder | A61B 8/08 324/71.4 |
| 6,467,331 B1 | * | 10/2002 | Kline-Schoder | A61B 8/08 239/9 |
| 6,629,449 B1 | * | 10/2003 | Kline-Schoder | A61B 8/08 356/243.2 |
| 6,806,947 B1 | * | 10/2004 | Ekdahl | A61M 1/3626 356/339 |
| 8,539,812 B2 | * | 9/2013 | Stringham | G01N 29/032 73/1.82 |
| 8,646,309 B2 | * | 2/2014 | Stringham | G01N 29/032 73/1.82 |
| 8,739,601 B2 | * | 6/2014 | Stringham | G01N 29/032 73/19.03 |
| 9,228,919 B1 | * | 1/2016 | Hawwa | G01M 3/08 |
| 2008/0297766 A1 | * | 12/2008 | Gengler | G01N 21/85 356/51 |
| 2017/0356838 A1 | * | 12/2017 | Knollenberg | G01F 1/704 |

* cited by examiner

Go to FIG. 3B

SYSTEM AND METHOD OF DETECTING WITHIN A LIQUID FLOW OF A PIPE

BACKGROUND OF THE INVENTION

Field the Invention

This invention relates to optical detectors. Specifically, and not by way of limitation, the present invention relates to a system for detecting abnormalities bubbles within a liquid flow in a pipe.

Description of the Related Art

There are various instances where it is necessary to analyze liquids for the presence of bubbles. For example, the analysis of blood is used to determine the presence of bubbles which may attach to blood or form air emboli which can be very harmful to patients. In various other applications and industry, it is desirable to be aware of the existence of bubbles in a liquid.

There are some existing detectors for utilized in detecting bubbles. Although there are no known prior art teachings of an apparatus or method such as that disclosed herein, prior art references that discusses subject matter that bears some relation to matters discussed herein are Patent Cooperation Treaty (PCT) Publication WO2017201451 to Knollenberg et al. (Knollenberg), U.S. Pat. No. 5,083,862 to Rusnak (Rusnak), U.S. Pat. No. 5,960,129 to Kleinschmitt (Kleinschmitt), U.S. Pat. No. 4,763,525 to Cobb (Cobb), and U.S. Pat. No. 3,812,482 to Clark (Clark).

Knollenberg does utilize conventional bubble detectors for detecting bubbles but does not teach or suggest the use of an infrared (IR) transmitter and receiver to detect the bubbles. Rusnak discloses a bubble detector utilizing a light emitter and detector. However, Rusnak discloses the emitter and detector being located offset from each other without a direct beam being transmitted between the two components. Rusnak fails to teach or suggest an IR transmitter and receiver located in line with one another. Kleinschmitt discloses the use of a couple of light sources and detectors for detecting bubbles. However, Kleinschmitt fails to teach or suggest an IR transmitter and receiver detecting the interruption of the modulated infrared optical signal pattern and works on the data collected with intervals. In addition, Cobb discloses the use of an ultrasonic bubble detector. However, Cobb fails to teach or suggest using an IR transmitter or receiver. Clark discloses the use of a light emitting diode and a photodetector which are disposed on opposite ends of an optical path oriented at an angle with respect to a substantially transparent blood conduit. Clark utilizes defracting techniques to detect the presence of gas or liquid. Clark fails to teach or suggest using an IR transmitter and receiver detecting the interruption of the modulated infrared optical signal pattern and works on the data collected with intervals.

A system and method are needed which utilizes a programmable microcontroller to easily change the working parameters of a given installation, now or in the future without the need to replace the electronical parts or the software that is running on the microcontroller. Furthermore, a system is needed which modulates IR light, thereby easily filtering unwanted light sources from other sources, thus preventing false reception/interruption signals and enhancing the accuracy of the detection system. It is an object of the present invention to provide such a system and method.

SUMMARY OF THE INVENTION

In one aspect, the present invention is a system for detecting bubbles within a liquid flowing in an interior of a pipe. The system includes a transmitter emitting directed light through the liquid flowing through the pipe and a receiver for receiving the emitted directed light from the transmitter. The transmitter and receiver are affixed on opposite sides of a wall of the pipe. The system also includes a microcontroller having a modulator. The microcontroller communicates with the transmitter and receiver. Additionally, the microcontroller sends a modulation protocol for emitting the directed light with a specified modulation protocol to the transmitter and receiver. The transmitter emits the directed light as modulated light based upon the modulation protocol and the receiver filters out all unmodulated light, correlates information on modulated light received from the transmitter and sends correlated light information to the microcontroller. The microcontroller then determines a presence of bubbles in the liquid based on the light information received from the receiver.

In another aspect, the present invention is a method of detecting bubbles within a liquid flowing in an interior of a pipe. The method begins by affixing a directed light transmitter to a first side of the pipe and a receiver to a second side opposite the first side on the pipe. Next, the microcontroller sends a modulation protocol for emitting a specific type of directed light to the transmitter and the receiver. The transmitter then emits directed light through the liquid in the pipe using the modulation protocol. The receiver then receives the emitted light from the transmitter and filters out all unmodulated light received by the receiver. Next, the receiver correlates information on the modulated light received from the transmitter and sends the correlated light information to the microcontroller. The microcontroller then determines a presence of bubbles in the liquid based on the light information received from the receiver.

DESCRIPTION OF THE INVENTION

Figure 1:
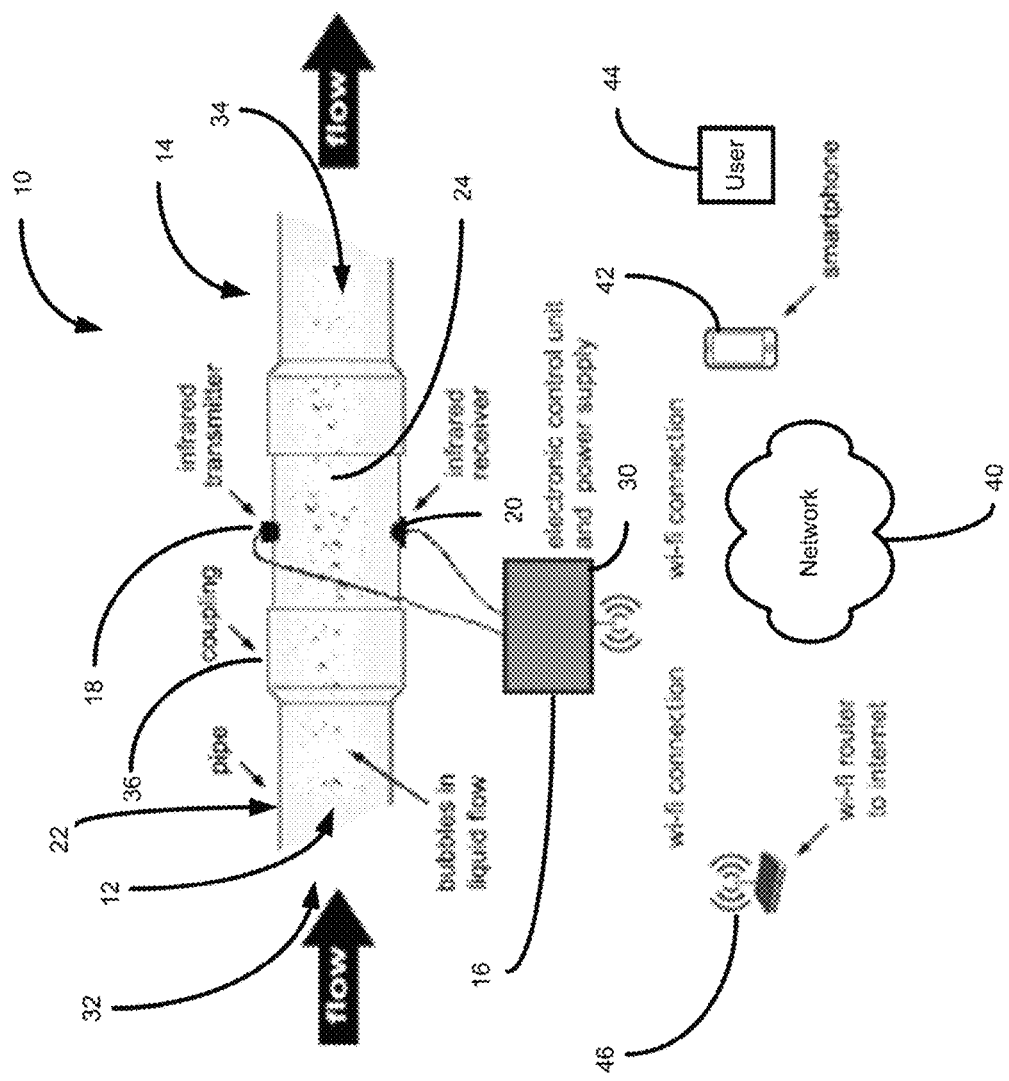
FIG. 1 is a simplified block diagram illustrating major components of a detection system for detecting bubbles within a liquid flow in a pipe.

The present invention is a system and method of detecting bubbles within a liquid flow in a pipe. FIG. 1 is a simplified block diagram illustrating major components of a detection system 10 for detecting bubbles 24 within a liquid 12 flow in a pipe 14. The system includes an electronic control unit 16 communicating with one or more infrared transmitters 18 and one or more infrared receivers 20. The infrared transmitter 18 is affixed to an outer surface 22 of the pipe 14. Likewise, on an opposing side from the infrared transmitter is positioned and affixed the infrared receiver 20. The electronic control unit 16 and the infrared receiver and transmitter are powered by a power supply 30. The power supply 30 may be separate units or utilize the same unit to power the electronic control unit 16, the infrared transmitter 18 and the infrared receiver 20. The infrared transmitter 18 may utilized a light-emitting diode (LED) for transmitting a directed beam to the infrared receiver 20. The pipe may be any conduit allowing a flow of the liquid 12. The pipe 14 includes a flow 32 through an interior 34 of the pipe. As illustrated, the pipe may include one or more couplings 36. In one embodiment of the present invention, the electronic control unit 16 may communicate through a wi-fi router 46 to a network 40, such as the Internet to a personal communication device (e.g., a mobile phone 42). A user 44 may send inputs, such as commands and parameters, and receive information through the mobile phone 42 from the electronic control unit 16.

Figure 2:
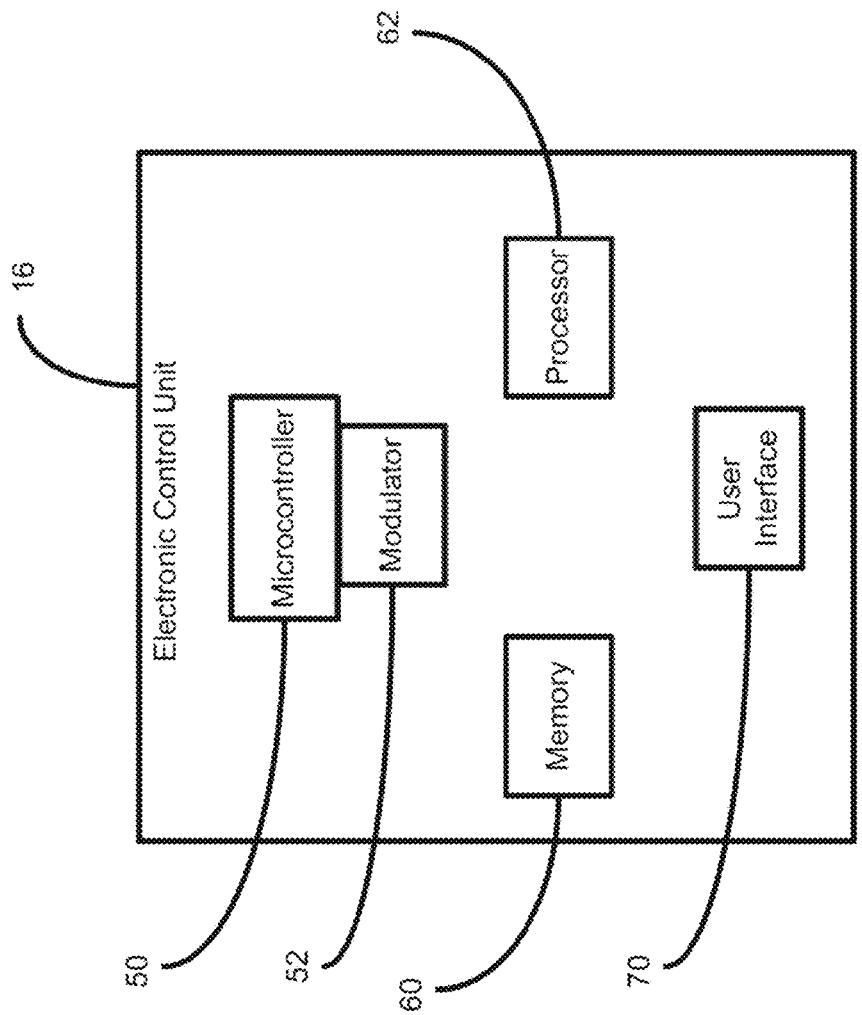
FIG. 2 is a simplified block diagram illustrating the components of the electronic control unit in one embodiment of the present invention.

FIG. 2 is a simplified block diagram illustrating the components of the electronic control unit 16 in one embodiment of the present invention. The electronic control includes a microcontroller 50 having a modulator 52. The microcontroller 50 may also include a memory 60 for storing a set of instructions and a processor 62 for executing the instructions. The processer 62 may access information from, and store information in a nonremovable memory, a removable memory, or a combination thereof, also collectively referred to herein as computer readable media. Illustrative nonremovable memory may consist of RAM, ROM, a hard disk, or other well-known memory storage technologies. Illustrative removable memory may consist of one or more Subscriber Identity Module (SIM) cards, or other well-known memory storage technologies, such as "smart cards," magnetic disks, floppy disks, optical disks, magneto-optical disks, magnetic tapes, or any suitable non-volatile memory. As will be discussed below, the set of instructions executed by the processor permit the control of the microcontroller 50 and the modulator 52. The electronic control unit 16 may also include a user interface 70 for interfacing with the user 44. The user interface may provide a Guided User Interface (GUI) for display on the mobile phone 42 or other communication device utilized by the user 44. The user interface 70 enables the user 44 to receive information from the electronic control unit 16 as well as allow the user to send commands to the electronic control unit 16.

The pipe 14 includes a flow 32 of liquid 12 within its interior 34. The pipe includes a first hole positioned on one side of the pipe and a second hole positioned on the opposite side of the pipe, abeam each other. The infrared transmitter 18 is attached to the pipe 14 at the first hole, while the infrared transmitter 20 is affixed at the second hole. In this configuration, the infrared transmitter 18 emits an infrared beam into the interior 34 of the pipe to the other side where the receiver 20 is situated. The infrared receiver 20 is in such a position to receive the infrared beam emitted by the infrared transmitter 18. Thus, the infrared beam passes through the liquid 12 flowing through the interior of the pipe. The microcontroller 50 controls the infrared transmitter 18 and, through the modulator 52, adjusts the intensity and pattern of the infrared beam. Furthermore, the microcontroller communicates with the infrared receiver 20 to obtain the results of receiving the emitted infrared beam.

In one embodiment, the microcontroller 50, through the modulator 52, adjusts the intensity and pattern of the emitted infrared beam from the infrared transmitter 18 (modulation). To accomplish the modulation of the infrared beam, the microcontroller may include a set of instructions stored in the memory 60 and executed by the processor 62 to command a digital potentiometer to change its resistance, which changes the current flowing through the infrared transmitter and emitted beam, which is in series with the digital potentiometer, thereby changing the intensity of the light that the infrared transmitter emits. The infrared receiver 20 may then send an acknowledgement signal to the microcontroller provided that the receiver is illuminated with sufficient infrared light and correct light frequency. Furthermore, the microcontroller may also command the infrared transmitter 18 to switch on and off repetitively, thus changing the pattern of the light emitted through time. Since the microcontroller also reads the output of the infrared receiver 20, the microcontroller may automatically adjust to provide the best light disruption performance to detect any entity in the water flow. By varying in the intensity and pattern of emitted infrared light, the detection of bubbles in the liquid flow may be enhanced. The on/off frequency and pattern of infrared light has been incorporated to filter out other infrared light sources, such as sun or florescent lights. The infrared receiver 20 incorporates filters to filter out all other continuous light sources or sources of infrared light with a different on/off frequency, intensity, etc. While the infrared receiver 20 is illuminated with the infrared beam emitted from the transmitter 18 with a predetermined correct on/off frequency and sufficient amount of light, the receiver's output is held on a high voltage state. If that received infrared light is even briefly disrupted or refracted enough such that the amount of light that falls upon the infrared receiver 20 is below a specified threshold, its output drops to a low voltage. These output voltage levels are constantly checked by the microcontroller.

With reference to FIGS. 1 and 2, the operation of the detection system 10 will now be explained. First, holes are placed on opposing sides of the pipe 14. The infrared transmitter 18 is affixed over the first hole and the infrared receiver 20 is affixed over the second hole. The transmitter and receiver are positioned in such a fashion as the emitted infrared beam from the transmitter 18 strikes the infrared receiver 20, with the beam passing through the interior 34 of the pipe and through the passing liquid 12. A modulation protocol is established and sent by the microcontroller 50 to the transmitter 18 and the receiver 20. The microcontroller, through the modulator 52, modulates the infrared light emitted from the transmitter 18 in a predetermined and specified manner. Modulation as discussed in the present invention may include the change in frequency, intensity, spectrum, turning the light off/on (pulsing), or any other fashion which would provide a distinction on the type of light transmitted and received by the transmitter and receiver. The microcontroller, through the processor, is programmable to change parameters and the modulation protocol as desired as well as initiating trigger events when specific thresholds are reached. The present invention may be utilized for any application where the detection of the presence of bubbles or other fluid abnormalities is required. In one application, the present invention may be utilized for detecting bubbles in a swimming pool filtration system. The specified modulation is known by both the transmitter and receiver. By knowing the modulation protocol, the receiver can filter out extraneous light sources. The microcontroller, through the modulator 52, modulates the infrared light emitted from the transmitter 18 in a predetermined and specified manner. As required, the transmitter emits the modulated infrared beam to the receiver. The receiver 20 receives the emitted modulated infrared light. As the receiver is aware of the proper modulation protocol, as received from the microcontroller, all other extraneous light sources are filtered from the receiver. The receiver obtains the data on the received light and correlates the data and sends the information on the received infrared light in accordance with the modulation protocol to the microcontroller. The microcontroller, through the processor 62, calculates the presence of bubbles by detecting the interruption of the modulated infrared optical signal pattern. For example, if bubbles were not present in the pipe, the modulated infrared beam would be received uninterrupted by the receiver 20. The receiver 20 would send receipt of the infrared light to the microcontroller. As the light is determined to be received uninterrupted, the microcontroller determines that there are no bubbles present in the pipe. However, when bubbles do pass through the emitted light, between the transmitter 18 and receiver 20, the emitted light beam is interrupted or distorted. The receiver receives interrupted or corrupted light. This information of a disruption of the beam is sent to the microcontroller. The microcontroller than determines that the interrupted light signals received by the receiver 20 indicate the presence of bubbles. Optional and customizable trigger events may be created and stored within the electronic control unit 16 as desired by the user. The trigger events are fully customizable and allow the user to select a specific threshold, cycle, or other relevant data event for use relevant in detecting the bubbles. The processed data and customizable trigger events are then sent through the network 40 to other communication devices, such as the mobile phone 42 or some other device, such as a laptop computer, a desktop computer, a tablet, etc. A Message Queuing Telemetry Transport (MQTT) cloud service via the local router 46 may be utilized. The parameters of the program on the microcontroller can also be accessed and modified via internet by other computing and/or communication devices.

Figure 3A:
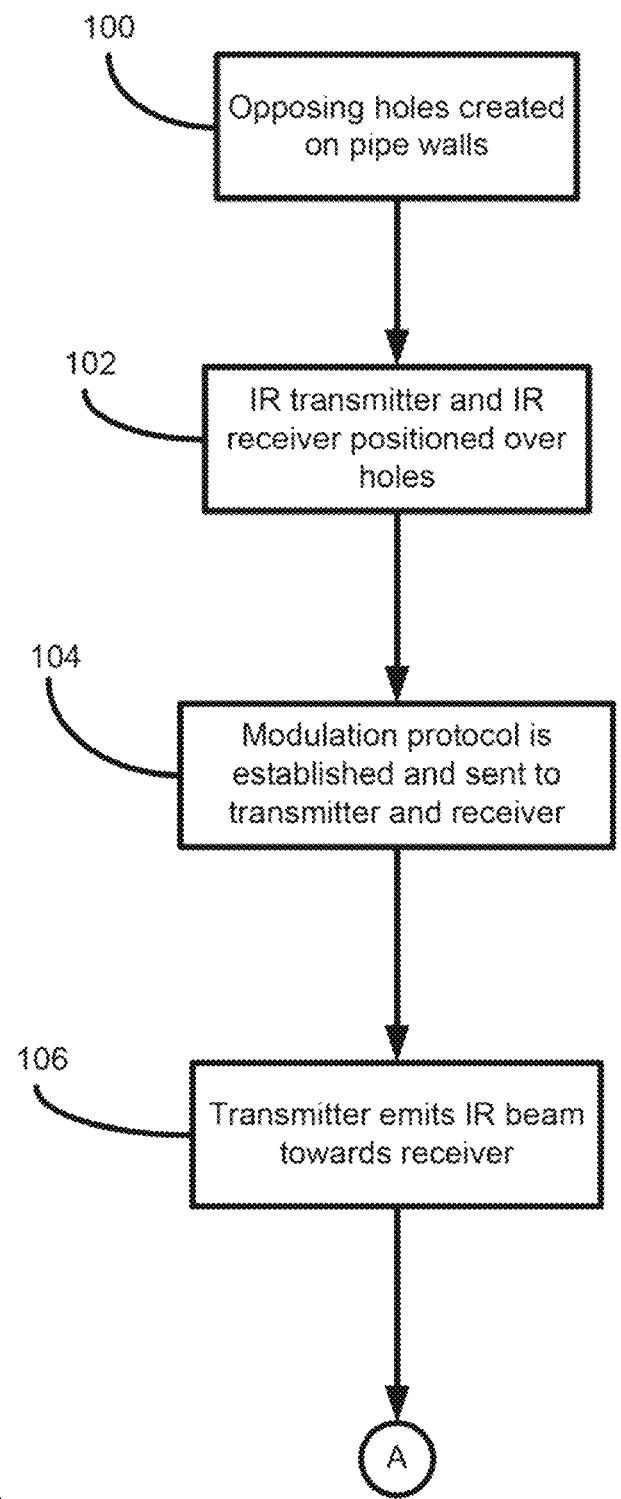
FIGS. 3A and 3B are flow charts illustrates the steps of detecting bubbles in the pipe using the detection system according to the teachings of the present invention.
Figure 3B:
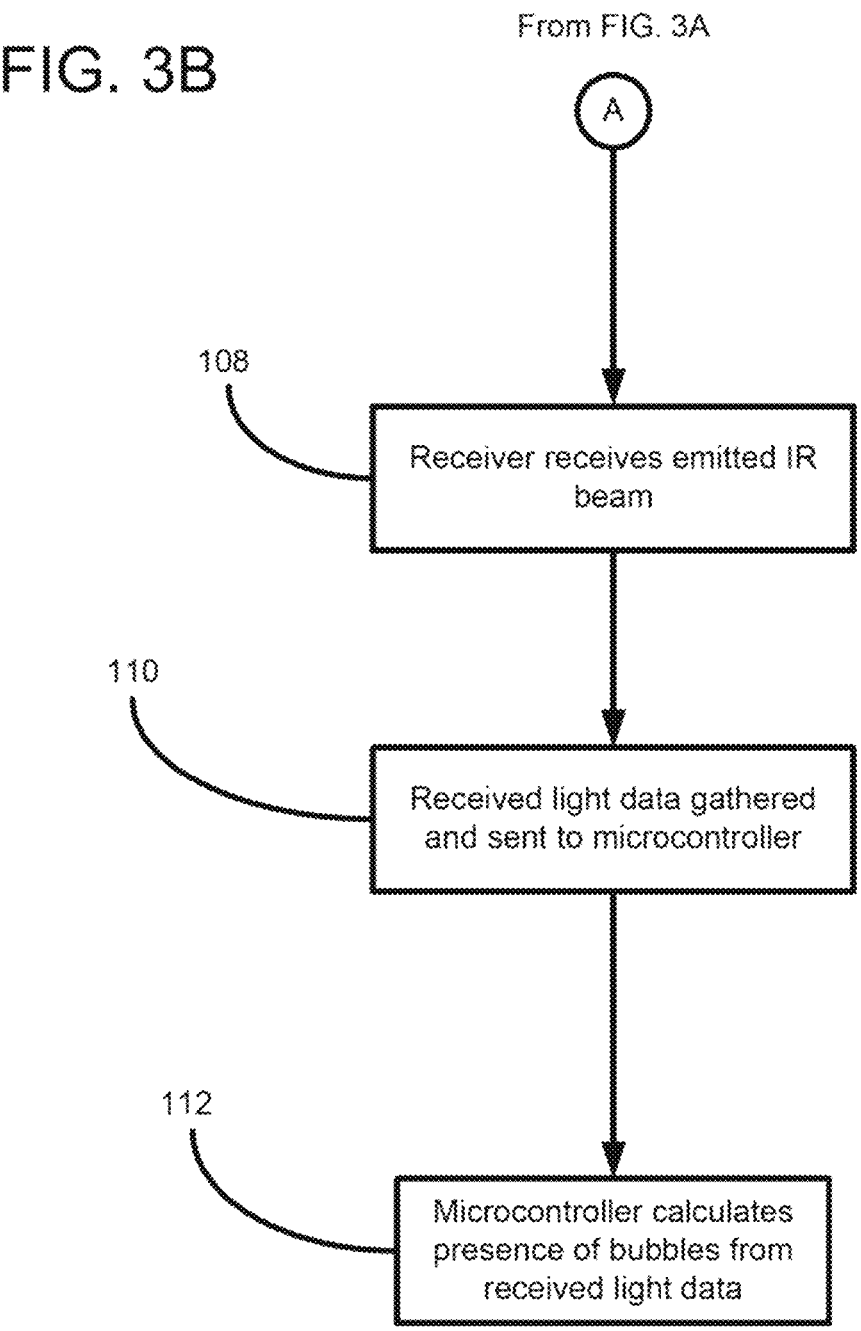

FIGS. 3A and 3B are flow charts illustrates the steps of detecting bubbles in the pipe 14 using the detection system 10 according to the teachings of the present invention. With reference to FIGS. 1-3, the steps of the method will now be explained. The method begins with step 100 where holes are created on opposing sides of the wall of the pipe 14. Next, in step 102, the infrared transmitter 18 is affixed over the first hole and the infrared receiver 20 is affixed over the second hole. The transmitter and receiver are positioned in such a fashion as the emitted infrared beam from the transmitter 18 strikes the infrared receiver 20, with the beam passing through the interior 34 of the pipe and through the passing liquid 12. Next, in step 104, a modulation protocol is established and sent by the microcontroller 50 to the transmitter 18 and the receiver 20. The microcontroller, through the modulator 52, modulates the infrared light emitted from the transmitter 18 in a predetermined and specified manner. Modulation as discussed in the present invention may include the change in frequency, intensity, spectrum, turning the light off/on, or any other fashion which would provide a distinction on the type of light transmitted and received by the transmitter and receiver. The specified modulation is known by both the transmitter and receiver. By knowing the modulation protocol, the receiver can filter out extraneous light sources not meeting the modulation protocol. Next, in step 106, the transmitter 18 emits the modulated infrared light towards the receiver 20. In step 108, the receiver 20 receives the emitted infrared light. In step 110, the received light data is obtained and correlated by the receiver and sent to the microcontroller 50. Next, in step 112, the microcontroller, through the processor 62, calculates the presence of bubbles by detecting the interruption of the modulated infrared optical signal pattern derived from the received light data. For example, if bubbles were not present in the pipe, the modulated infrared beam would be received uninterrupted by the receiver 20. The receiver 20 would send this receipt of the uninterrupted infrared light to the microcontroller. As the light is determined to be received uninterrupted, the microcontroller determines that there are no bubbles present in the pipe. However, when bubbles do pass through the emitted light, between the transmitter 18 and receiver 20, the emitted light beam is interrupted or distorted. The receiver receives interrupted or corrupted light. This information of a disruption of the beam is used by the microcontroller to determine whether there is the presence of bubbles. Optional and customizable trigger events are created and stored within the electronic control unit 16 as desired to provide follow on actions as necessary (e.g., sending alerts to the user through the mobile phone 42). The processed data and customizable trigger events are then sent through the network 40 to other communication devices, such as the mobile phone 42 or some other device such as a laptop computer, a desktop computer, a tablet, etc. A Message Queuing Telemetry Transport (MQTT) cloud service via the local router 46 may be utilized. The parameters of the program on the microcontroller can also be accessed and modified via internet by other computing and/or communication devices.

Although modulated infrared light beams are discussed in the present invention, the present invention may utilize other directed and distinct light sources having a defined signature and still remain in the scope of the present invention. Additionally, although the use of holes is discussed for use in emitting light through the interior of the pipe, the present invention may utilize any mechanism or type of pipe which does not require the placement of holes, such as transparent pipe.

The present invention provides many advantages over existing systems. The present invention provides a system for detecting bubbles which is accurate and is adaptable to conditions as necessary. The present invention utilizes modulated light providing a modulation protocol which provides a distinct signature for emitted light. Thus, the present invention is not corrupted by other light sources, thereby enhancing accuracy of the system. Additionally, the present invention utilizes a programmable microcontroller which enables a user to easily change the parameters of the detection system without replacing electronic components.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. A system for detecting bubbles within a liquid flowing in an interior of a pipe, the system comprising:
    a transmitter emitting directed light through the liquid flowing through a pipe, the transmitter affixed to a first side of the pipe;

a receiver for receiving the emitted directed light from the transmitter, the receiver affixed to a second side opposite the first side of the pipe; and a microcontroller having a modulator, the microcontroller communicating with the transmitter and receiver;

wherein the microcontroller sends a modulation protocol for emitting the directed light with a specified modulation protocol to the transmitter and receiver;

wherein the transmitter emits the directed light as modulated light based upon the modulation protocol;

wherein the receiver filters out all unmodulated light, correlates information on modulated light received from the transmitter and sends correlated light information to the microcontroller;

wherein the microcontroller determines a presence of bubbles in the liquid based on the light information received from the receiver.

2. The system according to claim 1 wherein the directed light is infrared light.

3. The system according to claim 1 wherein the light information correlated by the receiver includes information on when the received light is interrupted, the interruption indicating the presence of bubbles.

4. The system according to claim 1 wherein the liquid flowing through the pipe is water.

5. The system according to claim 1 wherein the modulation protocol includes modulation techniques varying frequency, intensity, spectrum, or pulsing of the directed light.

6. The system according to claim 1 wherein the pipe includes:
a first hole on a first side of a wall of the pipe; and
a second hole on a second side of the wall of the pipe;
wherein on the transmitter is positioned over the first hole and the receiver is positioned over the second hole.

7. The system according to claim 1 further comprising a communication device communicating with the microcontroller via a network.

8. The system according to claim 7 wherein the communication device provides instruction and receives information from the microcontroller.

9. The system according to claim 1 wherein the microcontroller is programmable for changing parameters of the modulation protocol.

10. The system according to claim 1 wherein the microcontroller executes an action based on a trigger event received from the light information received from the receiver.

11. A method of detecting bubbles within a liquid flowing in an interior of a pipe, the method comprising the steps of:
affixing a directed light transmitter to a first side of the pipe;
affixing a receiver to a second side opposite the first side on the pipe;
sending, by a microcontroller communicating with the transmitter and the receiver, a modulation protocol for emitting a specific type of directed light to the transmitter and the receiver;
emitting directed light using the modulation protocol, by the transmitter, through the liquid flowing through a pipe;
receiving, by the receiver, the emitted light from the transmitter;
filtering out, by the receiver, all unmodulated light received by the receiver;
correlating, by the receiver, information on modulated light received from the transmitter;
sending correlated light information to the microcontroller; and
determining, by the microcontroller, a presence of bubbles in the liquid based on the light information received from the receiver.

12. The method according to claim 11 wherein the directed light is infrared light.

13. The method according to claim 11 wherein the light information correlated by the receiver includes information on when the received light is interrupted, the interruption indicating the presence of bubbles.

14. The method according to claim 11 wherein the liquid flowing through the pipe is water.

15. The method according to claim 11 wherein the modulation protocol includes modulation techniques varying frequency, intensity, spectrum, or pulsing of the directed light.

16. The method according to claim 11 further comprising the step of communicating, by the microcontroller, with a communication device via a wireless network.

17. The method according to claim 16 wherein the communication device provides instruction and receives information from the microcontroller.

18. The method according to claim 11 further comprising the step of changing the modulation protocol.

19. The method according to claim 11 further comprising the step of executing an action by the microcontroller, based on a trigger event received from the light information received from the receiver.

* * * * *

UNITED STATES PATENT AND TRADEMARK OFFICE
CERTIFICATE OF CORRECTION

PATENT NO. : 10,352,866 B1
APPLICATION NO. : 15/948995
DATED : July 16, 2019
INVENTOR(S) : Mehmet Arbatli Page 1 of 1

It is certified that error appears in the above-identified patent and that said Letters Patent is hereby corrected as shown below:

On the Title Page

Item [54], "SYSTEM AND METHOD OF DETECTING WITHIN A LIQUID FLOW OF A PIPE" should read -SYSTEM AND METHOD OF DETECTING BUBBLES WITHIN A LIQUID FLOW OF A PIPE-.

Signed and Sealed this
Third Day of September, 2019

Andrei Iancu
*Director of the United States Patent and Trademark Office*